United States Patent [19]

Moser et al.

[11] Patent Number: 5,128,371
[45] Date of Patent: Jul. 7, 1992

[54] ACYLATED NAPHTHLAMINES AS PLANT FUNGICIDES

[75] Inventors: Hans Moser, Magden, Switzerland; Wolfgang Eckhardt, Lörrach, Fed. Rep. of Germany; Walter Kunz, Oberwil, Switzerland; Adolf Hubele, Magden, Switzerland

[73] Assignee: Ciba-Geigy Corporation, Ardsley, N.Y.

[21] Appl. No.: 731,356

[22] Filed: Jul. 15, 1991

Related U.S. Application Data

[63] Continuation of Ser. No. 570,995, Aug. 21, 1990, abandoned, which is a continuation of Ser. No. 391,657, Aug. 8, 1989, abandoned, which is a continuation of Ser. No. 63,707, Jun. 15, 1987, abandoned, which is a continuation of Ser. No. 820,272, Jan. 16, 1986, abandoned, which is a continuation of Ser. No. 358,490, Mar. 15, 1982, abandoned, which is a continuation of Ser. No. 195,222, Oct. 8, 1980, abandoned, which is a continuation-in-part of Ser. No. 138,066, Apr. 7, 1980, abandoned.

[30] Foreign Application Priority Data

Apr. 10, 1979 [CH] Switzerland ............... 3404/79

[51] Int. Cl.$^5$ ............... A01N 43/08; C07D 307/20
[52] U.S. Cl. .................................. 514/472; 549/320
[58] Field of Search ............... 514/472; 549/320

[56] References Cited

U.S. PATENT DOCUMENTS 4,316,909 2/1982 Kunz et al. ............... 514/473

FOREIGN PATENT DOCUMENTS 871668 4/1979 Belgium .
2008576 6/1979 United Kingdom .

*Primary Examiner*—Nicky Chan
*Attorney, Agent, or Firm*—Marla J. Mathias; Edward McC. Roberts

[57] ABSTRACT

There are described novel acylated naphthylamines of the formula I defined herein

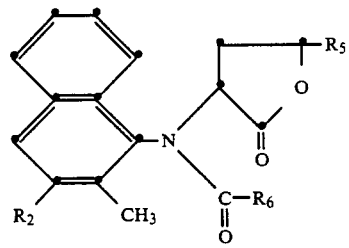

which have valuable fungicidal properties. They can be used in practice on their own or in the form of compositions for the protection of cultivated plants against fungus infection.

15 Claims, No Drawings

ACYLATED NAPHTHLAMINES AS PLANT FUNGICIDES

This application is a continuation of Ser. No. 570,995, filed Aug. 21, 1990, now abandoned, which in turn is a continuation of Ser. No. 391,657, filed Aug. 8, 1989, now abandoned, which in turn is a continuation of Ser. No. 063,707, filed Jun. 15, 1987, now abandoned, which in turn is a continuation of Ser. No. 820,272, filed Jan. 16, 1986, now abandoned, which in turn is a continuation of Ser. No. 358,490, filed [February] Mar. 15, 1982, now abandoned, which in turn is a continuation of Ser. No. 195,222, filed Oct. 8, [1982,]1980, now abandoned, which in turn is a continuation-in-part of Ser. No. 138,066, filed Apr. 7, 1980, now abandoned.

The present invention relates to compounds of the formula I

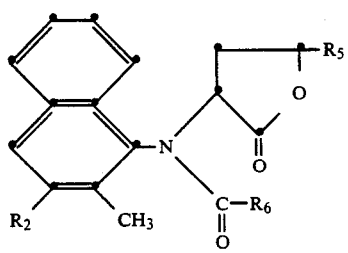

wherein $R_2$ is hydrogen or methyl; $R_5$ is hydrogen or methyl; and $R_6$ is 2-furyl or 2-tetrahydrofuryl each of which is unsubstituted or is substituted by halogen, or $R_6$ is $\beta$-($C_1$-$C_4$)-alkoxyethyl or the group $CH_2Z$, where Z is one of the groups a) —X—$R_7$, b) —NH—N($R_8$)($R_9$), c) —$OSO_2R_{10}$, d) —O(CO)$R_{11}$, e) 1,2-pyrazole or f) 1,2,4-triazole (1), including the salts and metal complexes thereof, and X is oxygen or sulfur, $R_7$ is a $C_1$-$C_6$-alkyl group substituted by $C_1$-$C_2$-alkoxy, or it is $C_3$-$C_4$-alkenyl or $C_3$-$C_4$-alkynyl, $R_8$ is hydrogen or $C_1$-$C_3$-alkyl, $R_9$ is $C_1$-$C_3$-alkyl or phenyl, $R_{10}$ is $C_1$-$C_4$-alkyl or mono- or di-($C_1$-$C_3$)-alkylamine, and $R_{11}$ is $C_1$-$C_3$-alkyl which is unsubstituted or is substituted by $C_1$-$C_2$-alkoxy.

By alkyl or as alkyl moiety of another substituent are meant, depending on the given number of C atoms, the following groups: methyl, ethyl, propyl, butyl, pentyl and hexyl, as well as isomers thereof, such as iso-propyl, iso-butyl, sec-butyl, tert-butyl and iso-pentyl. Alkenyl is for example allyl or 2-butenyl. Alkynyl is in particular propargyl. $C_3$-$C_7$-cycloalkyl embraces cyclopropyl, cyclobutyl, cyclopentyl, cyclohexyl and cycloheptyl. Halogen is fluorine, chlorine, bromine or iodine.

As metal cations in complexes of compounds of the formula I, there are preferably used those from the main groups II and IV as well as from the subgroups I, II and IV to VIII of the periodic system, for example: Mg, Ca, Ba, Sn, Pb, Cu, Zn, Cd, Cr, Mn, Fe, Co and Ni.

Suitable salt-binding acids for the compounds of the formula (I) are those having good plant tolerance. They include the hydrohalic acids (such as hydrochloric acid and hydrobromic acid), also sulfuric acid, phosphoric acid, nitric acid, mono- and bifunctional carboxylic acids and hydroxycarboxylic acids, for example acetic acid, tartaric acid, citric acid, salicyclic acid, lactic acid, 1,5-naphthalene-disulfonic acid, methanesulfonic acid, benzenesulfonic acid, and so forth.

The compounds of the formula I can be produced by a whole series of methods, such as by those given in the following under A-F. In the formulae II to XVI, the symbols $R_2$ to $R_{11}$ and X have the meanings defined under the formula I, "Hal" is halogen, preferably chlorine or bromine, and M is hydrogen or a metal cation, preferably an alkali metal cation or alkaline-earth metal cation.

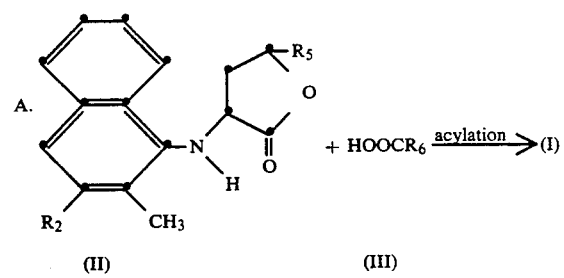

A reactive derivative of the carboxylic acid of the formula III can advantageously be used, for example the acid halide, acid anhydride or the ester. A suitable acid halide is in particular the acid chloride or acid bromide.

The use of acid-binding agents and condensation agents is in some cases of advantage. Suitable as such are for example: tertiary amines such as trialkylamines (for example triethylamine), pyridine and pyridine bases or inorganic bases, such as the oxides, hydroxides, hydrogen carbonates, carbonates or hydrides of alkali metals and alkaline-earth metals, as well as sodium acetate. The starting product II can also serve as acid-binding agent.

The production process A can also be performed without acid-binding agents; in some cases it is then advisable to pass nitrogen through in order to expel the formed hydrogen halide. In other cases, an addition of dimethylformamide as a reaction catalyst is very advantageous.

B. When $R_6$ is —$CH_2OSO_2R_{10}$ or —$CH_2$—O(CO)$R_{11}$, it is possible, after preliminary acylation of a compound of the formula II with hydroxyacetic acid (or with a derivative thereof) to formula IV, to perform the following variant:

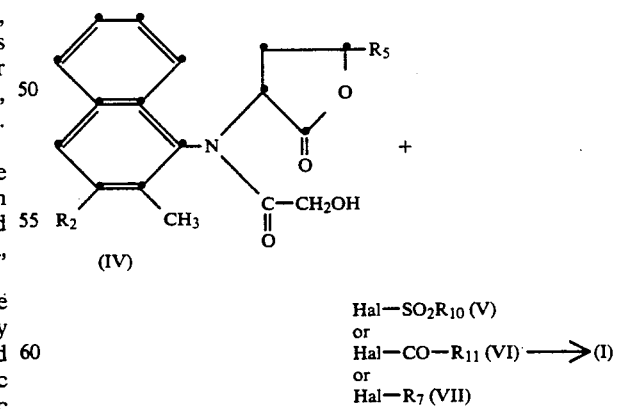

With the reaction variant B, a salt (=alcoholate), particularly an alkali salt of the compound of the formula IV, is advantageously used. This process is carried out if necessary in the presence of an acid-binding agent, such as one of those described under A.

C. Where $R_6$ has a meaning other than —CH$_2$N-H—N(R$_8$) (R$_9$), it is possible also to perform the following process variant:

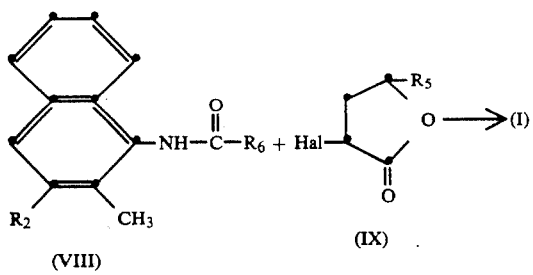

The compound of the formula VIII is in this case firstly converted with butyl-lithium, sodium carbonate or sodium hydride into the corresponding N-alkali salt, or alternatively the process is carried out in the presence of an acid-binding agent in a manner analogous to that of process A, preferably with the addition of a catalytic amount of alkali iodide.

D. When $R_6$ is —CH$_2$XR$_7$, —CH$_2$—O—CO—R$_{11}$, —CH$_2$NH—N(R$_8$) (R$_9$) or an azolylmethyl group (azole=1,2-pyrazole or 1,2,4-triazole), it is possible to perform, after preliminary haloacetylation of a compound of the formula II to formula X, the following variant:

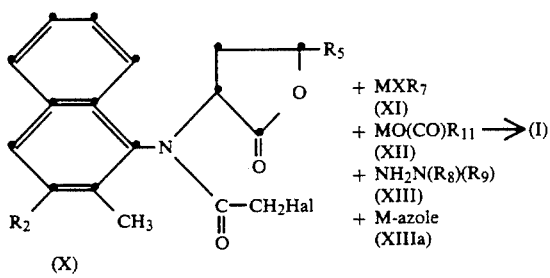

Where M is hydrogen, the use of a salt-forming agent is appropriate, for example an oxide, hydroxide or hydride of alkali metals or alkaline-earth metals. With use of starting materials of the formula XIII or XIIIa, the final product is obtained as hydrohalide. From this can be obtained using mild bases, at room temperature or at slightly elevated temperature, the free hydrazino or azole base. Alkali carbonates for example are suitable for this purpose.

E. When $R_6$ is β-(C$_1$-C$_4$)-alkoxyethyl:

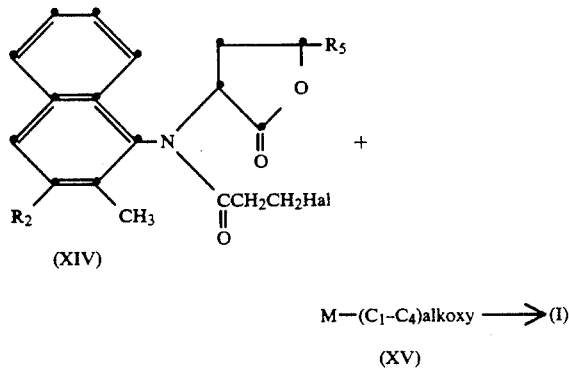

F. When $R_6$ is β-(C$_1$-C$_4$)-alkoxyethyl:

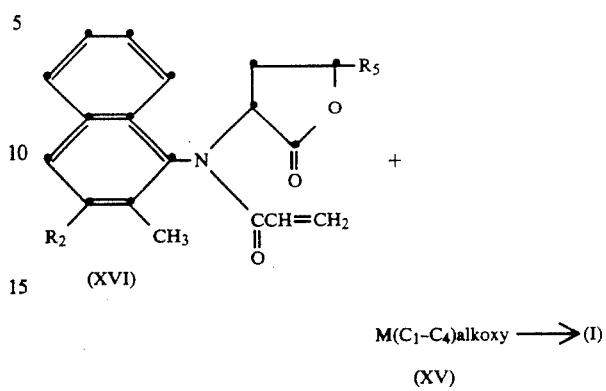

A Michael's reaction is performed in this process with the alcohol or with the alcoholate XV (M=metal atom).

Solvents which have to be inert to the reactants can be used in all processes. Examples of suitable solvents are: hydrocarbons such as benzene, toluene, xylenes or petroleum ether; halogenated hydrocarbons such as chlorobenzene, methylene chloride, ethylene chloride or chloroform; ethers and ethereal compounds such as dialkyl ether, dioxane or tetrahydrofuran; nitriles such as acetonitrile; N,N-dialkylated amides such as dimethyl formamide; dimethyl sulfoxide, ketones such as methyl ethyl ketone, and mixtures of solvents of this type with each other.

The various processes are included in the subject matter of the present invention.

Some of the starting materials are novel and are also embraced by the invention. They are produced by methods known per se and likewise exhibit fungicidal activity.

The compounds of the formula I contain in the lactone moiety an asymmetrical carbon atom, and can be split in the customary manner into optical antipodes, for example by fractional crystallisation of the salt formed from a compound of the formula II and an optically active acid, and further reaction of the resulting optical antipode of formula II to an enantiomer of the formula I. These exhibit differing microbicidal activities.

Further asymmetrical carbon atoms can occur in the molecule depending on substitution.

Owing to the presence of an asymmetric carbon atom in the lactone moiety and the steric hindrance about the

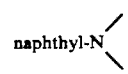

axis, the synthesis of compounds of the formula I usually leads to diastereomeric mixtures. This yields, by separate processing, products having different physical characteristics.

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.1 and 90%.

For application, the compounds of the formula I can be in the following forms (the weight-percentage figures in brackets signify advantageous amounts of active substance):

solid preparations dusts and scattering agents (up to 10%), granulates [coated granules, impregnated granules and homogeneous granules] and pellets (1 to 80%);

liquid preparations a) water-dispersible concentrates of active substance: wettable powders and pastes (25 to 90% in the commercial packing, 0.01 to 15% in ready-for-use solutions); emulsion concentrates and solution concentrates (10 to 50%; 0.01 to 15% in ready-for-use solutions);

b) solutions (0.1 to 20%); aerosols.

Preparations of this type are also embraced by the invention.

In the Belgian Patent Specification No. 871,668 are mentioned in a general form acetamides as fungicides, with individual mention of those compounds which are derived from α-naphthylamine. A typical representative of this series, N-(2-methylnaphthyl)-N-(2-oxo-tetrahydrofuran-3-yl)-N-methoxyacetylamine, is designated in the reproduced tests as being ineffectual, completely in contrast to the fungicidally effective analogous representatives of the phenylamine group (=aniline group). This disclosure of the Belgian Patent Specification No. 871,668 gives to a person skilled in the art no indication of the existence of highly effective fungicides within the group of acylated α-napthylamines of the formula I of the present invention. It has been shown surprisingly that within this group novel highly effective plant fungicides are obtained only by combination of specific structural elements, as is shown with respect to the formula I of the present invention, particularly the combination of the groups denoted by $R_6$ with the lactone side chain. Combinations of this type produce fungicides which are particularly tolerant to plants without causing unpleasant secondary effects. Active substances of the formula I are furthermore characterised by a distinct lasting action.

Accordingly, the present invention relates to the following subgroups of acylated α-naphthylamines of formula I:

| | | |
|---|---|---|
| a) | —CO—CH$_2$—X—R$_7$ | aliphatic acyl compounds, |
| b) | —CO—CH$_2$—NH—N(R$_8$)(R$_9$) | hydrazinoacetyl derivatives, |
| c) | —CO—CH$_2$—O—SO$_2$R$_{10}$ | sulfonyl- and sulfamoyl-acetyl derivatives, |
| d) | —CO—CH$_2$—O—COR$_{11}$ | acylated hydroxyacetyl derivatives, |
| e) | —CO—CH$_2$—N⟨pyrazole⟩ | pyrazolyl-acetyl derivatives (and salts and metal complexes thereof), |
| f) | —CO—CH$_2$—N⟨triazole⟩ | triazolyl-acetyl derivatives (and salts and metal complexes thereof), |
| g) | | optionally halogenated furanoyl and tetrahydrofuranoyl derivatives, and |
| h) | | β-alkoxy-propionyl derivatives. |

The above subgroups are to be understood together with the remaining portion of the chemical structure of formula I and the respective definitions given for $R_2$ to $R_{11}$ and X.

It has been found that surprisingly compounds having the structure of the formula I exhibit a very favourable microbicidal spectrum for practical requirements for the protection of cultivated plants. Cultivated plants within the scope of the present invention are for example: cereals, maize, rice, vegetables, sugar beet, soya bean, groundnuts, fruit trees and ornamental plants, but particularly grape vines, hops, Cucurbitaceae (cucumbers, pumpkins and melons), Solanaceae, such as potatoes, tobacco and tomatoes, as well as bananas, cocoa and natural rubber plants.

Fungi occurring on plants or on parts of plants (fruit, blossom, foliage, stalks, tubers, roots or rice seedlings) of the said crops and of related crops can be inhibited or destroyed with the active substances of the formula I, and also parts of plants subsequently growing remain preserved from such fungi. The active substances are effective against phytopathogenic fungi belonging to the following classes: Ascomycetes (for example Erysiphaceae, Sclerotinia and Helminthosporium); Basidiomycetes, such as in particular rust fungi; Rhizoctonia; Fungi imperfecti (for example Moniliales and Piricularia); and particularly against Oomycetes belonging to the Phycomycetes class, such as Phytophthora, Peronospora, Pseudoperonospora, Pythium or Plasmopara. Furthermore, the compounds of the formula I have a systemic action. They can also be used as dressing agents for the treatment of seed (fruit, tubers and grain), and of plant cuttings (for example rice seedlings) to protect them against fungus infections, and also against phytopathogenic fungi occurring in the soil.

The invention thus relates also to the use of the compounds of the formula I for combating phytopathogenic microorganisms.

The following types of substituents and combinations thereof with each other are preferred:

$R_2$ is hydrogen or methyl, $R_5$ is hydrogen or methyl, $R_6$ is 2-furyl or 2-tetrahydrofuryl or —CH$_2$Z, the meaning of Z being a) OR$_7$ b) —NH—N(R$_8$) (R$_9$), c) —OSO$_2$R$_{10}$, or d) 1,2,4-triazole and salts and metal complexes thereof, wherein R$_7$ is β-methoxyethyl, allyl or propargyl; and R$_8$ and R$_9$ independently of one another are each C$_1$-C$_2$-alkyl, and R$_{10}$ is C$_1$-C$_2$-alkyl or monomethylamine.

In the group of unsaturated aliphatic acyl compounds, the following representatives as fungicides are particularly preferred:

A-1) N-(2-propin-1-yloxyacetyl)-N-(2-methylnaphthyl)-N-(2-oxo-tetrahydrofuran-3-yl)-amine [=compound 5], A-2) N-(2-propin-1-yloxyacetyl)-N-2,3-di-methylnaphthyl)-N-(2-oxo-tetrahydrofuran-3-yl)-amine [=compound 31].

In the group of saturated aliphatic acyl compounds, the following representative as fungicide is particularly preferred:

B-1) N-(2,3-dimethylnaphthyl)-N-(p-methoxy-ethoxyacetyl)-N-(2-oxo-tetrahydrofuran-3-yl)-amine [=compound 32].

In the group of sulfonylated and sulfamoylated acyl compounds, the following representatives as fungicides are particularly preferred:

C-1) N-methylsulfonyloxyacetyl-N-(2-methylnaphthyl)-N-(2-oxo-tetrahydrofuran-3-yl)-amine [compound 15], C-2) N-(N'-methylsulfamoyloxyacetyl)-N-(2-methylnaphthyl)-N-(2-oxo-tetrahydrofuran-3-yl)-amine [=compound 18], C-3) N-(2,3-dimethylnaphthyl)-N-(N'-methylsulfamoyloxyacetyl)-N-(2-oxo-tetrahydrofuran-3-yl)-amine [compound 26], and C-4) N-(2,3-dimethylnaphthyl)-N-(methylsulfonyloxyacetyl)-N-(2-oxo-tetrahydrofuran-3-yl)-amine [=compound 25].

In the group of triazolylacetyl compounds, the following representative as fungicide is particularly preferred:

D-1) N-(2,3-dimethylnaphthyl)-N-(2-oxo-tetrahydrofuran-3-yl)-N-[1,2,4-triazolyl(1)-acetyl]-amine [=compound 22].

In the group of furanoyl and tetrahydrofuranoyl compounds, the following representatives as fungicides are particularly preferred:

E-1) N-(2-methylnaphthyl)-N-(2-oxo-tetrahydrofuran-3-yl)-N-[tetrahydrofuranoyl(2)]-amine [=compound 6], E-2) N-(2,3-dimethylnaphthyl)-N-(2-oxo-tetrahydrofuran-3-yl)-N-[tetrahydrofuranoyl(2)]-amine [compoun 21].

The following Examples serve to further illustrate the invention without limiting its scope. Temperature values are given in degrees Centigrade, and percentages and parts relate to weight. Except where otherwise stated, the naming of an active substance of the formula I is to be taken in all cases as meaning the isomeric mixture.

PRODUCTION EXAMPLES

EXAMPLE 1 Production of

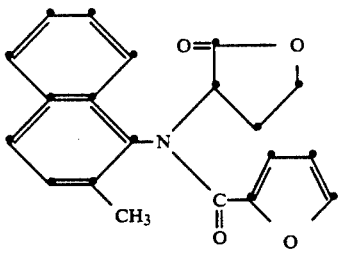

N-(2-methylnaphthyl)-N-(2-oxo-tetrahydrofuran-3-yl)-N-(2-furanoyl)-amine [=compound 1].

a) 78.5 g of 1-amino-2-methylnaphthalene, 90.8 g of 2-bromo-4-butyrolactone and 53 g of sodium carbonate in 250 ml of dimethylformamide are stirred at 70° for 40 hours; the mixture is cooled and filtered, and the solvent is evaporated off in vacuo. The oily residue is taken up in 1000 ml of methylene chloride, washed three times with 200 ml of water each time, dried over sodium sulfate and filtered, and the methylene chloride is evaporated off. The residue is taken up in diethyl ether, treated with active charcoal, filtered, and cooled to effect crystallisation. The precipitate is filtered off, and subsequently purified by recrystallisation from methanol to yield 3-[N-(2-methylnaphthyl)]-amino-tetrahydro-2-furanone, m.p. 89°–91°.

b) 12 g of the intermediate obtained according to a), 13.7 g of furan-2-carboxylic acid chloride and 5.8 g of sodium carbonate are stirred at 60° C. for 24 hours; the mixture is then cooled and filtered, and the filtrate is washed with 200 ml of sodium carbonate solution and twice with 200 ml of water each time; it is subsequently dried over sodium sulfate and filtered, and the solvent is evaporated off. After recrystallisation from ethyl acetate/petroleum ether, the crystals of the diastereoisomeric mixture melt at 141°–166°.

EXAMPLE 2 Production of

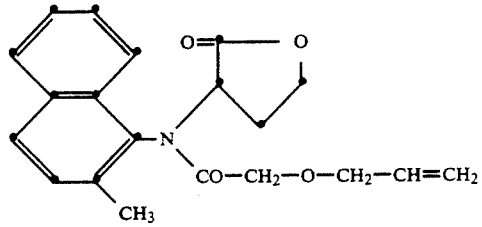

N-(2-methylnaphthyl)-N-(2-oxo-tetrahydrofuran-3-yl)-N-allyloxyacetylamine [=compound 11].

14.5 g of 3-[N-2-methylnaphthyl(1)-amino]-butyrolactone and 9.3 g of allyloxyacetyl chloride in 100 ml of absolute toluene are refluxed in an $N_2$ atmosphere for 4 hours. After the evolution of HCl has ceased, the solvent is evaporated off. The brown oil remaining is taken up in 200 ml of toluene, treated with active charcoal and filtered. After concentration of the solution by evaporation, the diastereoisomeric mixture of compound 11 remains as a semisolid substance, $n_D^{22} = 1.5911$.

EXAMPLE 3 Production of

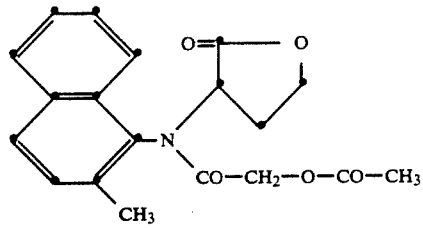

N-(2-methylnaphthyl)-N-(2-oxo-tetrahydrofuran-3-yl)-N-acetoxyacetylamine [=compound 19].

A mixture of 18.2 g of N-(2-methylnaphthyl)-N-(2-oxo-tetrahydrofuran-3-yl)-N-chloroacetyl-amine, 11.5 g of anhydrous sodium acetate and 0.1 g of KJ in 70 ml of dimethylformamide (DMF) is heated at 110° for 16 hours. The reaction mixture is afterwards cooled to room temperature, poured into 200 ml of water and extracted three times with 50 ml of ethyl acetate each time. The combined extracts are washed with 50 ml of water, dried over sodium sulfate, filtered and then concentrated by evaporation. The dark-brown oil remaining is purified through silica gel 60 (particle size 0.06–0.2 mm) using chloroform/diethyl ether (1:1) as the eluant. The last 10 of 12 fractions are combined and the eluant is evaporated off. The diastereoisomeric mixture of the compound No. 19 which remains solidifies on cooling, m.p. 50°–70°.

EXAMPLE 4 a) Production of N-(2-methylnaphthyl)-N-(2-oxo-tetrahydrofuran-3-yl)-N-hydroxyacetylamine (intermediate).

16.3 g of the compound No. 19 produced in Example 3 are dissolved at room temperature in 100 ml of absolute methanol, and 1 g of 25% sodium methylate is added, and the desired intermediate commences to precipitate after 5 minutes. After 2 hours' stirring, the brown crystalline powder obtained is filtered off and then washed with methanol, m.p. 191°–195°.

b) Production of

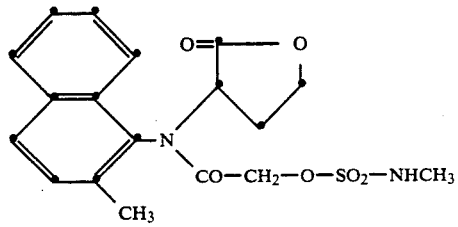

N-(2-methylnaphthyl)-N-(2-oxo-tetrahydrofuran-3-yl)-N-(N'-methyl-sulfamoyloxyacetyl)-amine [=compound 18].

7.1 g of methylamine-N-sulfonic acid chloride, dissolved in 20 ml of absolute acetonitrile, are added dropwise at room temperature to 15 g of the intermediate produced under a) in admixture with 4.3 g of pyridine and 80 ml of absolute acetonitrile, in the course of which the reaction mixture warms up to 35°. After 12 hours' stirring at room temperature, a further 3.2 g of pyridine and 5.2 g of methylamine-N-sulfonic acid chloride are added. After 2 hours' stirring, the reaction mixture is concentrated by evaporation; the residue is then taken up in 200 ml of ethyl acetate, washed with 50 ml of water, dried over sodium sulfate and filtered. The solvent is evaporated off, and the oil remaining is brought to crystallisation with diethyl ether. The crystalline diastereoisomeric final product is recrystallised, in the presence of active charcoal, from 500 ml of ethanol, m.p. 190°–194°.

EXAMPLE 5 Production of

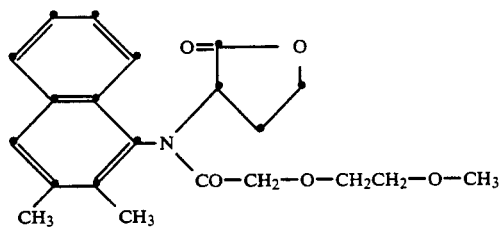

N-(2,3-dimethylnaphthyl)-N-(2-oxo-tetrahydrofuran-3-yl)-N-(2-methoxy-ethoxy-acetyl)-amine [compound 32].

To 15.3 g of N-(2,3-dimethylnaphtyl)-N-(2-oxo-tetrahydrofuran-3-yl)-amine in 120 ml of toluene are added dropwise 12.2 g of 2-methoxyethoxy-acetyl chloride (MAC) in 20 ml of toluene and afterwards 8.1 g of triethylamine in 20 ml of toluene. The temperature of the reaction rises to 35° and is then raised to 40° for 2 hours. There are subsequently added dropwise a further 2 g of MAC and 1.5 g of triethylamine. The temperature is held overnight at 40°, and afterwards a further 2 g of MAC are added dropwise. After 4 hours, the reaction mixture is cooled to room temperature and filtered, and the filtrate is concentrated by evaporation to yield a resinous residue, which is purified through silica gel 60 using ethyl acetate as the eluant. The solid product occurring from the residue is recrystallised from isopropanol with the addition of active charcoal. The resulting product is the colourless diastereoisomeric mixture of the compound No. 32, m.p. 142°–146°.

The following compounds of the formula I are produced in an analogous manner or by one of the methods described herein.

TABLE

| Comp. No. | $R_2$ | $R_6$ | $R_5$ | Physical constants |
|---|---|---|---|---|
| 1 | H | (2-oxo-tetrahydrofuran-3-yl) | H | m.p. 141–166° |
| 2 | H | (2-oxo-tetrahydrofuran-3-yl) | $CH_3$ | m.p. 138–149° |
| 3 | H | (2-oxo-4-bromo-tetrahydrofuran-3-yl) | H | m.p. 165–210° |
| 4 | H | $-CH_2NH-NH-\text{phenyl}$ | H | oil |
| 5 | H | $-CH_2OCH_2C\equiv CH$ | H | $n_D^{23.5}$: 1.5971 |

TABLE-continued

| Comp. No. | R₂ | R₆ | R₅ | Physical constants |
|---|---|---|---|---|
| 6 | H | (furanyl-type ring with H, O) | H | m.p. 179–205° |
| 7 | H | —CH₂CH₂OCH₃ | H | m.p. 137,5–140° |
| 8 | H | —CH₂N(1,2,4-triazol-1-yl) | H | m.p. 75–100° |
| 9 | H | —CH₂—NHN(CH₃)₂ | H | oil |
| 10 | H | —CH₂—N(pyrazol-1-yl) | H | oil |
| 11 | H | —CH₂OCH₂CH=CH₂ | H | $n_D^{22}$: 1,5911 |
| 12 | H | —CH₂—OSO₂N(CH₃)₂ | H | m.p. 133–170° |
| 13 | H | —CH₂N(1,2,4-triazol-1-yl) · ½H₂SO₄ | H | m.p. >280° |
| 14 | H | —CH₂N(1,2,4-triazol-1-yl) | CH₃ | m.p. 68–86° |
| 15 | H | —CH₂—OSO₂CH₃ | H | m.p. 182–191° |
| 16 | H | —CH₂—NHN(CH₃)₂ | CH₃ | brown oil |
| 17 | H | —CH₂N(1,2,4-triazol-1-yl) · ½CuCl₂ | H | m.p. >300° |
| 18 | H | —CH₂—OSO₂NHCH₃ | H | m.p. 190–194° |
| 19 | H | —CH₂—OC(O)CH₃ | H | m.p. 50–70° |
| 20 | CH₃ | (furan ring with O) | H | m.p. 197–199° |
| 21 | CH₃ | (furanyl-type ring with H, O) | H | m.p. 230–234° |
| 22 | CH₃ | —CH₂—N(1,2,4-triazol-1-yl) | H | diast. I m.p. 209–210°<br>diast. II m.p. 219–221°<br>diast. mixture m.p. 79–188° |
| 23 | CH₃ | —CH₂CH₂OCH₃ | H | m.p. 151–162° |
| 24 | CH₃ | —CH₂—NH—N(CH₃)₂ | H | oil |
| 25 | CH₃ | —CH₂—OSO₂CH₃ | H | m.p. 212–214° |
| 26 | CH₃ | —CH₂—OSO₂NHCH₃ | H | m.p. 144–146° |

TABLE-continued

| Comp. No. | $R_2$ | $R_6$ | $R_5$ | Physical constants |
|---|---|---|---|---|
| 27 | $CH_3$ | $-CH_2-OCCH_3$ (with C=O) | H | m.p. 213-215° |
| 28 | H | $-CH_2-O-C_2H_4-OCH_3$ | H | $n_D^{22}$ 1,5832 |
| 29 | H | $-CH_2O-SO_2NHC_2H_5$ | H | m.p. 143-145° |
| 30 | H | $-CH_2-O-C_2H_4-OC_2H_5$ | H | $n_D^{21,5}$ 1,5750 |
| 31 | $CH_3$ | $-CH_2-O-CH_2-C\equiv CH$ | H | m.p. 148-150° |
| 32 | $CH_3$ | $-CH_2-O-C_2H_4-O-CH_3$ | H | m.p. 142-146° |
| 33 | $CH_3$ | (bromofuryl group) | H | m.p. 201-209° |
| 34 | $CH_3$ | $-CH_2-O-CH_2-CH=CH_2$ | H | m.p. 92-99° |
| 35 | $CH_3$ | $-CH_2-O-C_2H_4-OC_2H_5$ | H | m.p. 124-126° |
| 36 | $CH_3$ | $-CH_2-O-SO_2NHC_2H_5$ | H | m.p. 130-132° |
| 37 | $CH_3$ | $-CH_2-OSO_2N(CH_3)_2$ | H | m.p. 145-162° |

Formulation Examples

EXAMPLE 1

Dust: The following substances are used to produce a) a 5% dust and b) a 2% dust:
a) 5 parts of active substance, and
95 parts of talcum;
b) 2 parts of active substance,
1 part of highly dispersed silicic acid, and
97 parts of talcum.

The active substances are mixed and ground with the carriers, and in this form they can be applied by dusting.

EXAMPLE 2

Granulate The following substances are used to produce a 5% granulate:

5 parts of active substance,
0.25 part of epoxidised vegetable oil,
0.25 part of cetyl polyglycol ether,
3.50 parts of polyethylene glycol, and
91 parts of kaolin (particle size 0.3-0.8 mm).

The active substance is mixed with epoxidised vegetable oil and dissolved in 6 parts of acetone, and the polyethylene glycol and cetyl polyglycol ether are then added. The solution obtained is sprayed onto kaolin, and the acetone is evaporated off in vacuo. A microgranulate of this type is advantageously used for combating soil fungi.

EXAMPLE 3

Wettable powder: The following constituents are used to produce a) a 70% wettable powder, b) a 40% wettable powder, c) and d) a 25% wettable powder, and e) a 10% wettable powder:
a) 70 parts of active substance,
5 parts of sodium dibutylnaphtylsulfonate,
3 parts of naphthalenesulfonic acid/phenolsulfonic acid/formaldehyde condensate (3:2:1),
10 parts of kaolin, and
12 parts of Champagne chalk;
b) 40 parts of active substance,
5 parts of sodium lignin sulfonate,
1 part of sodium dibutylnaphthylsulfonate, and
54 parts of silicic acid;
c) 25 parts of active substance,
4.5 parts of calcium lignin sulfonate,
1.9 parts of Champagne chalk/hydroxyethyl cellulose mixture (1:1),
1.5 parts of sodium dibutylnaphthylsulfonate,
19.5 parts of silicic acid,
19.5 parts of Champagne chalk, and
28.1 parts of kaolin;
d) 25 parts of active substance,
2.5 parts of isooctylphenoxy-polyoxyethylene-ethanol,
1.7 parts of Champagne chalk/hydroxyethylcellulose mixture (1:1),
8.3 parts of sodium aluminium silicate,
16.5 parts of kieselgur, and
46 parts of kaolin; and
e) 10 parts of active substance,
3 parts of a mixture of the sodium salts of saturated fatty alcohol sulfates,
5 parts of naphthalenesulfonic acid/formaldehyde condensate, and
82 parts of kaolin.

The active substances are intimately mixed in suitable mixers with the additives, and the mixture is then ground in applicable mills and rollers. There are obtained wettable powders which have excellent wetting and suspension properties, which can be diluted with water to give suspensions of the concentration required, and which in this form are particularly suitable for leaf application.

EXAMPLE 4

Emulsifiable concentrate

The following substances are used to produce a 25% emulsifiable concentrate:
25 parts of active substance,
2.5 parts of epoxidised vegetable oil,
10 parts of an alkylarylsulfonate/fatty alcohol polyglycol ether mixture,
5 parts of dimethylformamide, and
57.5 parts of xylene.

Emulsions of the concentration desired can be prepared from these concentrates by dilution with water, and they are particularly suitable for leaf application.

Biological Examples

1. Action against Phytophthora infestans on tomato plants a) Residual protective action

Three weeks after being sown, tomato plants were sprayed with a spray liquor prepared from wettable powder of the active substance (0.02% and 0.006%, respectively, of active substance). After 24 hours, the treated plants were infested with a sporangia suspension of the fungus. An assessment of fungus infection was made after incubation of the infested plants for 5 days at 20° with 90-100% relative humidity.

b) Residual curative action

Tomato plants were infested, after three weeks' cultivation, with a sporangia suspension of the fungus. After an incubation time of 22 hours in a moist chamber at 20° with 90-100% relative humidity, the infested plants were dried, and then sprayed with a spray liquor prepared from wettable powder of the active substance (0.02% and 0.006%, respectively, of active substance). After the applied coating had dried, the treated plants were returned to the moist chamber. An assessment of fungus infection was made 5 days after infestation. With an application concentration of 0.02% or of 0.006% (*) in tests a) and b), the following compounds reduced fungus infection to 0-5%: 1, 2, 3, 4, 5, 6*, 7, 8*, 9*, 10, 11, 12, 13, 14*, 15*, 16*, 17*, 18*, 20, 21*, 22*, 23, 24*, 25, 26*, 27*, 28, 29*, 30, 31*, 32*, 33, 34*, 35, 36*, 37*.

c) Systemic action

A spray liquor produced from wettable powder of the active substance (0.006% of active substance, relative to the volume of soil) was applied to the surface of the soil of three-week-old tomato plants. Care was taken to ensure that the spray liquor did not come into contact with the parts of the plants above the soil. After 48 hours, the treated plants were infested with a sporangia suspension of the fungus. The assessment of fungus infection was made after incubation of the infested plants for 5 days at 20° with 90-100% relative humidity. All the active substances listed with respect to tests a) and b) prevented, by virtue of the systemic action of the compounds, occurrence of disease on the plants. The plants displayed a healthy appearance.

2. Action against Plasmopara viticola on grape vines

Young grape-vine seedlings in the 4-5-leaf stage were sprayed with a spray liquor produced from wettable powder of the active substance (0.02% of active substance). After 24 hours, the treated plants were infested with a sporangia suspension of the fungus. After an incubation of 6 days at 20° with 95-100% relative humidity, an assessment of fungus infection was made.

The active substances listed in the biological Example 1 and also the active substance No. 19 prevented fungus infection either completely or virtually completely (0-5% infection).

3. Action against Pythium debaryanum on carrots a) Action after soil application

The fungus was cultivated on a carrot-chips nutrient solution, and was then applied to a soil/sand mixture. The soil infested in this manner was placed into flower pots, and sown with sugar-beet seeds. Immediately after sowing, the test preparations, formulated from wettable powder, were applied as aqueous suspensions to the soil (20 ppm of active substance, relative to the volume of soil). The pots were then left for 2-3 weeks in a greenhouse at 20°. The soil during this time was maintained uniformly moist by careful watering with a watering-can.

b) Action after dressing application

The fungus was cultivated on a carrot-chips nutrient solution, and was then added to a soil/sand mixture. The soil infested in this manner was placed into soil trays, and sown with sugar-beet seeds which had been dressed with the test preparations formulated as dressing powders (0.06% of active substance). The sown trays were left for 2-3 weeks in a greenhouse at about 20°. The soil was maintained during this period uniformly moist by light watering.

For the evaluation of both tests, the percentage of sugar-beet plants which had emerged and also the proportion of healthy plants and diseased plants were determined.

All of the active substances listed in the preceding biological Examples 1 and 2 exhibited a complete action against Pythium spp. (over 90% of plants emerged). The plants had a healthy appearance.

4. Action against Cercospora arachidicola on groundnut plants 10-15 cm high groundnut plants were sprayed with a spray liquor prepared from wettable powder of the active substance (0.02% of active substance), and 48 hours later they were infested with a conidiospore suspension of the fungus. The infested plants were incubated for 72 hours at about 21° with high relative humidity, and were subsequently left in a greenhouse until the typical leaf spots appeared. An assessment of the fungicidal action was made 12 days after infestation and was based on the number and size of the occurring spots.

Compounds proving particularly highly effective against Cercospora infestation were, inter alia, those of the subgroups a)=aliphatic acyl compounds, c)=sulfonyl- and sulfamoyl-acetyl derivatives, e)=pyrazolyl-acetyl derivatives and f)=triazolyl-acetyl derivatives. Fungus infestation was almost completely prevented with the following compounds (0-10% infestation):

a) Nos. 5, 11, 31 and 34;
c) Nos. 18, 26, 29 and 36;
e) No. 10;
f) Nos. 13, 14, 17 and 22;
and also with the compound No. 21.

What is claimed is:

1. An acylated naphthylamine of the formula I

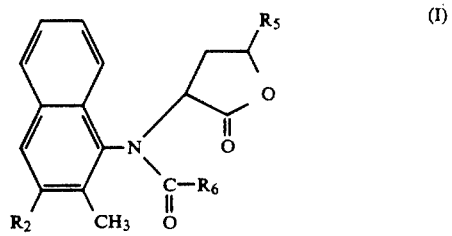

wherein $R_2$ is hydrogen or methyl; $R_5$ is hydrogen or methyl; and $R_6$ is 2-tetrahydrofuryl which is unsubstituted or substituted by halogen; including acid addition salts or metal complexes thereof.

2. An acylated naphthylamine of the formula I according to claim 1, wherein
$R_2$ is hydrogen or methyl,
$R_5$ is hydrogen or methyl, and
$R_6$ is, 2-tetrahydrofuryl.

3. An acylated naphthylamine of claim 1 selected from the group consisting of N-(2-methylnaphthyl)-N-(2-oxo-tetrahydrofuran-3-yl)-N-[tetrahydrofuranoyl(2)]-amine and N-(2,3-dimethylnaphthyl)-N-(2-oxo-tetrahydrofuran-3-yl)-N-[tetrahydrofuranoyl(2)]-amine.

4. N-(2-methylnaphthyl)-N-(2-oxo-tetrahydrofuran-3-yl)-N-[tetrahydrofuranoyl(2)]-amine according to claim 3.

5. N-(2,3-dimethylnaphthyl)-N-(2-oxo-tetrahydrofuran-3-yl)-N-[tetrahydrofuranoyl(2)]-amine according to claim 3.

6. A plant fungicidal composition which comprises a fungicidally effective amount of a compound of the formula I

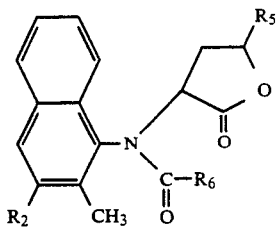

wherein $R_2$ is hydrogen or methyl; $R_5$ is hydrogen or methyl; and $R_6$ is 2-tetrahydrofuryl which is unsubstituted or substituted by halogen; including acid addition salts or metal complexes thereof; and a suitable carrier or surface active additive.

7. A plant fungicidal composition of claim 6 wherein the compound I is a compound wherein $R_6$ is unsubstituted 2-tetrahydrofuryl.

8. A plant fungicidal composition of claim 6 wherein the compound of formula I is selected from the group consisting of N-(2-methylnaphthyl)-N-(2-oxo-tetrahydrofuran-3-yl)-N-[tetrahydrofuranoyl(2)]-amine and N-(2,3-dimethylnaphthyl)-N-(2-oxo-tetrahydrofuran-3-yl)-N-[tetrahydrofuranoyl(2)]-amine.

9. A plant fungicidal composition of claim 6 wherein the compound of formula I is N-(2-methylnaphthyl)-N-(2-oxo-tetrahydrofuran-3-yl)-N-[tetrahydrofuranoyl(2)]-amine.

10. A plant fungicidal composition of claim 6 wherein the compound of formula I is N-(2,3-dimethylnaphthyl)-N-(2-oxo-tetrahydrofuran-3-yl)-N-[tetrahydrofuranoyl(2)]-amine.

11. A method of combating or preventing fungal infestation of plants which comprises applying, to the plant or the locus thereof, a fungicidally effective amount of a compound of the formula I

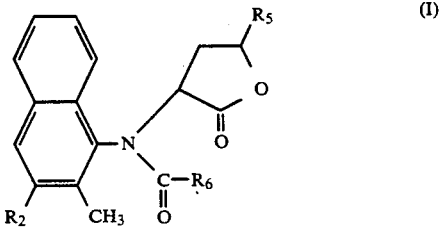

wherein $R_2$ is hydrogen or methyl; $R_5$ is hydrogen or methyl; and $R_6$ is 2-tetrahydrofuryl which is unsubstituted or substituted by halogen; including acid addition salts or metal complexes thereof.

12. A method of claim 11 wherein the compound of formula I is a compound wherein $R_6$ is unsubstituted 2-tetrahydrofuryl.

13. A method of claim 11 wherein the compound of formula I is selected from the group consisting of N-(2-methylnaphthyl)-N-(2-oxo-tetrahydrofuran-3-yl)-N-[tetrahydrofuranoyl(2)]-amine and N-(2,3-dimethylnaphthyl)-N-(2-oxo-tetrahydrofuran-3-yl)-N-[tetrahydrofuranoyl(2)]-amine.

14. A method of claim 11 wherein the compound of formula I is N-(2-methylnaphthyl)-N-(2-oxo-tetrahydrofuran-3-yl)-N-[tetrahydrofuranoyl(2)]-amine.

15. A method of claim 11 wherein the compound of formula I is N-(2,3-dimethylnaphthyl)-N-(2-oxo-tetrahydrofuran-3-yl)-N-[tetrahydrofuranoyl(2)]-amine.

* * * * *